United States Patent [19]
McAuliffe et al.

[11] Patent Number: 5,958,922
[45] Date of Patent: Sep. 28, 1999

[54] INSECTICIDAL MIXTURES

[75] Inventors: David McAuliffe, Newark; Isaac Billy Annan, Wilmington, both of Del.

[73] Assignee: E. I. du Pont de Nemours and Company, Wilmington, Del.

[21] Appl. No.: 09/142,724

[22] PCT Filed: Mar. 6, 1997

[86] PCT No.: PCT/US97/04106

§ 371 Date: Sep. 14, 1998

§ 102(e) Date: Sep. 14, 1998

[87] PCT Pub. No.: WO97/33476

PCT Pub. Date: Sep. 18, 1997

Related U.S. Application Data

[60] Provisional application No. 60/013,516, Mar. 15, 1996.

[51] Int. Cl.$^6$ .......................... A01N 43/64; A61K 31/535
[52] U.S. Cl. ........................................ 514/229.2; 514/242
[58] Field of Search .................... 514/229.2, 242

[56] References Cited

FOREIGN PATENT DOCUMENTS

| 2 720 230-A1 | 12/1995 | France . |
| 2720230 | 12/1995 | France . |
| 9211249 | 7/1992 | WIPO . |
| WO 92/11249 | 7/1992 | WIPO . |
| 9529171 | 11/1995 | WIPO . |
| WO 95/29171 | 11/1995 | WIPO . |

*Primary Examiner*—Allen J. Robinson

[57] ABSTRACT

This invention pertains to synergistic insecticidal mixtures of methyl 7-chloro-2,5-dihydro-2-[[(methoxycarbonyl)[4-(trifluoromethoxy)phenyl]amino]carbonyl]indeno[1,2-e][1,3,4]oxadiazine-4a(3H)-carboxylate and pymetrozine, and their agriculturally suitable compositions and method of use to control arthropod pests in general and insects specifically.

6 Claims, No Drawings

INSECTICIDAL MIXTURES

This application claims the benefit of U.S. Provisional Application No. 60/013,516, filed Mar 15, 1996.

This application is a 371 of PCT/US97/04106, filed Mar. 6, 1997.

BACKGROUND OF THE INVENTION

This invention pertains to synergistic insecticidal mixtures comprising combinations of methyl 7-chloro-2,5-dihydro-2-[[(methoxycarbonyl)[4-(trifluoro-methoxy)phenyl]amino]carbonyl]indeno[1,2-e][1,3,4]oxadiazine-4a (3H)-carboxylate and pymetrozine, their agriculturally suitable compositions and methods for the use of such compositions to control insect pests of plants.

Insecticide applications that can be applied at as low a dose as possible and be effective in controlling pest species of insects while causing as little harm as possible to beneficial insects and minimal disturbance in the environment are in demand by the farming community. Insects are very destructive to crop plants and can result in significant loss of crop yield and quality, which results in economic loss to the grower and increased costs to the consumer. Combinations of insecticides are typically used to broaden the spectrum of insect control or enhance the level of control of any given species through additive effect. Certain rare combinations surprisingly give a greater-than-additive or synergistic effect. Such a valuable combination has now been discovered.

FR 2720230-A1 discloses combinations of pymetrozine with certain classes of insecticides said to be synergistic. This reference does not disclose mixtures of pymetrozine with methyl 7-chloro-2,5-dihydro-2-[[(methoxycarbonyl)[4-(trifluoro-methoxy)phenyl]amino]carbonyl]indeno[1,2-e][1,3,4]oxadiazine4a(3H)-carboxylate, nor does it describe or suggest the remarkable synergistic efficacy of said mixtures.

SUMMARY OF THE INVENTION

This invention pertains to mixtures comprising methyl 7-chloro-2,5-dihydro-2-[[(methoxycarbonyl)[4-(trifluoromethoxy)phenyl]amino]carbonyl]indeno[1,2-e]-[1,3,4]oxadiazine-4a(3H)-carboxylate (Formula I), including the enantiomer (S)-methyl 7-chloro-2,5-dihydro-2-[[(methoxycarbonyl)[4-(trifluoromethoxy)phenyl]amino]-carbonyl]indeno[1,2-e][1,3,4]oxadiazine4a(3H)-carboxylate (Formula Ia) alone and in admixture with its antipode (R)-methyl 7-chloro-2,5-dihydro-2-[[(methoxycarbonyl)[4-(trifluoromethoxy)phenyl]amino]carbonyl]indeno[1,2-e][1,3,4]oxadiazine-4a(3H)-carboxylate (Formula Ib), in combination with pymetrozine ((E)-4,5-dihydro-6-methyl-4-[(3-pyridinylmethylene)amino]-1,2,4-triazin-3(2H)-one, Formula II), agricultural compositions containing them, and their use as insecticides.

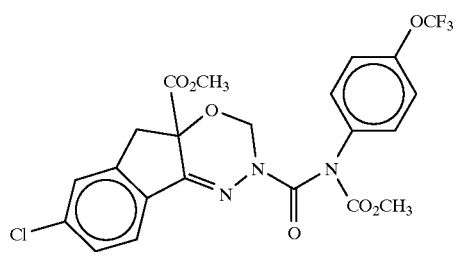

I

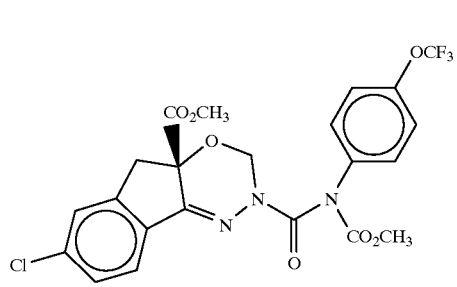

Ia

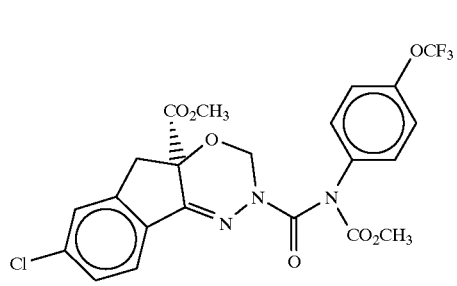

Ib

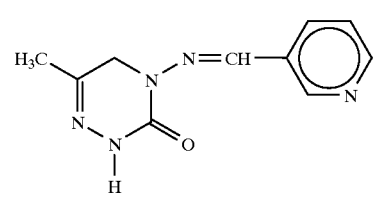

II

DETAILED DESCRIPTION OF THE INVENTION

Combinations of methyl 7-chloro-2,5-dihydro-2-[[(methoxycarbonyl)[4-(trifluoro-methoxy)phenyl]amino]carbonyl]indeno[1,2-e][1,3,4]oxadiazine-4a(3H)-carboxylate and pymetrozine have now been found to provide control of certain insects which is substantially and surprisingly enhanced over the expected simply additive control by said components.

Methyl 7-chloro-2,5-dihydro-2-[[(methoxycarbonyl)[4-(trifluoromethoxy)phenyl]-amino]carbonyl]indeno[1,2-e][1,3,4]oxadiazine4a(3H)-carboxylate (Formula I) is a foliar insecticide being developed by DuPont for control of numerous insect pests of agricultural crops including, but not limited to, insects from the order Lepidoptera (e.g., diamondback moth, cabbage looper, beet armyworm, fall armyworm, Heliothis spp.). Formula I also provides control or partial control and suppression of numerous insect pests of agricultural crops including, but not limited to, insects of the order Coleoptera (e.g., colorado potato beetle, weevils), Homoptera (e.g., aphids, leafhoppers), Hemiptera (e.g., plant bugs, stink bugs, lygus bugs), and Thysanoptera (e.g., thrips). The Formula I compound is particularly effective against Lepidopteran insects, on which it acts through both feeding and contact and has moderate residual properties.

Particularly useful for superior insecticidal activity and ease of manufacture and formulation is a 75:25 ratio of the enantiomer (S)-methyl 7chloro-2,5-dihydro-2-[[(methoxycarbonyl)[4-(trifluoromethoxy)phenyl]amino] carbonyl]indeno[1,2-e][1,3,4]-oxadiazine-4a(3H)-carboxylate (Formula Ia) in admixture with its antipode (R)-methyl 7-chloro-2,5-dihydro-2-[[(methoxycarbonyl)[4-(trifluoromethoxy)phenyl]amino]-carbonyl]indeno[1,2-e][1,3,4]oxadiazine-4a(3H)-carboxylate (Formula Ib). This enantiomeric mixture is also referred to as (S,R)-methyl 7-chloro-2,5-dihydro-2-[[(methoxycarbonyl)[4-(trifluoromethoxy)phenyl]amino]carbonyl]indeno[1,2-e][1,3,4]-oxadiazine4a(3H)-carboxylate 75:25 stereoisomer mixture.

Methyl 7-chloro-2,5-dihydro-2-[[(methoxycarbonyl)[4-(trifluoromethoxy)phenyl]-amino]carbonyl]indeno[1,2-e][1,3,4]oxadiazine4a(3H)-carboxylate (Formula I), including the enantiomers comprising it, can be prepared as described in WO 92/11249 and WO 95/29171. A synthesis involves the reaction of the amine of Formula 1 with the carbamyl chloride of Formula 2 in an inert solvent such as methyl acetate in the presence of a suitable base such as saturated aqueous sodium hydrogen carbonate.

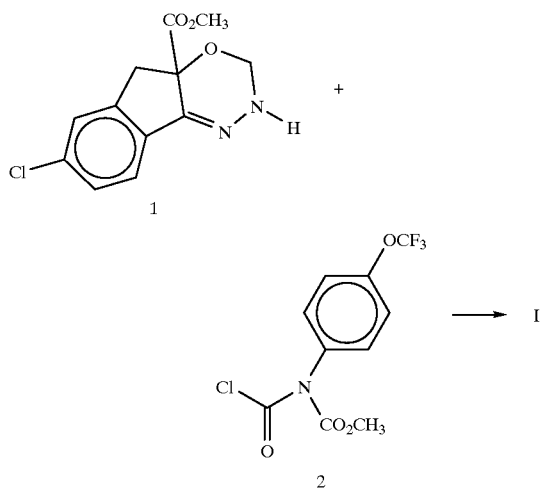

Pymetrozine is an insecticide product of Ciba-Geigy, marketed for the control of Homopterous insects including, but not limited to, aphids (e.g., *Aphis gossypii, Myzus persicae, Brevicoryne brassicae, Hydaphis pseudobrassicae, Acyrthosiphon pisum, Aphis craccivora, Aphis fabae, Macrosiphum rosae, Macrosiphum euphorbiae, Hyalopterus amygdali, Brachycaudus persicaecola, Aphis pomi, Sappaphis piricola, Aphis citricola, Toxoptera citricida, Toxoptera aurantii, Phorodon humuli*), whitefly (e.g., *Bemisia tabaci, Trialeurodes vaporariorum*), planthoppers (e.g., *Nilaparvata lugens, Laodelphax striatellus*), and leafhoppers (e.g., *Erythroneura sp.*). (See C. R. Fluckiger, H. Kristinsson, R. Senn, A. Rindlisbacher, H. Buholzer and G. Voss, "CGA 215'944—A novel agent to control aphids and whiteflies" in *Brighton Crop Protection Conference—Pests and Diseases*—1992, 2–3 pp. 43–50.)

Pymetrozine (Formula II) can be prepared as described in Canadian patent 1,325,211. A synthesis involves the condensation of the amine of Formula 3 with the aldehyde of Formula 4 in the presence of an acidic catalyst such as concentrated hydrochloric acid in a solvent such as ethanol heated under reflux.

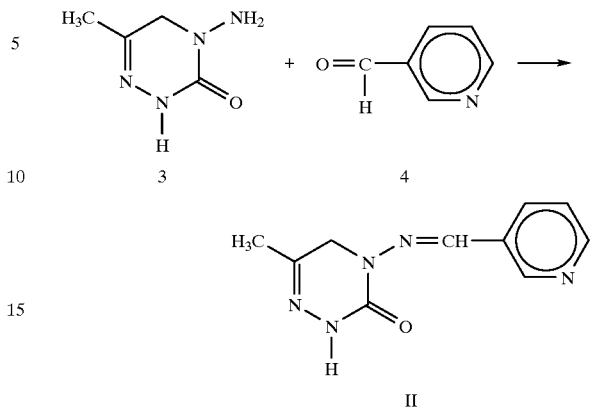

In the mixtures of this invention, pymetrozine can be present in the form of agriculturally suitable salts as described in published Canadian patent application 2,105,723. Agriculturally suitable salts of pymetrozine include acid addition salts. These salts are formed, for example, with strong inorganic acids, such as mineral acids, for example, sulfuric acid, nitric acid, phosphoric acid or a hydrohalic acid, with strong carboxylic acids, such as substituted or unsubstituted lower alkanecarboxylic acids, for example formic acid, acetic acid or trifluoroacetic acid, unsaturated or saturated dicarboxylic acids, for example oxalic, malonic, succinic, maleic, fumaric or phthalic acid, hydroxycarboxylic acids, for example ascorbic, lactic, malic, tartaric or citric acid, substituted or unsubstituted benzoic acid, for example 4-methylbenzoic acid, or with substituted or unsubstituted organic sulfonic acids, for example methane- or p-toluenesulfonic acid. In view of the close relationship between pymetrozine in free form and its agriculturally suitable salts, including their equilibration under physiological and environmental conditions, hereinbefore and hereinafter any reference to pymetrozine is to be understood as including both free pymetrozine and its agriculturally suitable salts, where appropriate and expedient. According to this invention, mixtures containing the free form of pymetrozine are, however, preferred.

Homopterous insects are severe pests of many field crops, vegetables, greenhouse crops, fruit trees and vines. Control of these insects is essential for quality crops and high yields. Combinations of insecticides are often used to gain control of the numerous species of Homopterous insects through additive effect. A few combinations may even be synergistic, providing significantly better pest control than could be predicted based on the activity of the individual components. Mixtures of the Formula I compound and pymetrozine have been found to exhibit surprising synergistic effects.

The pronounced synergism manifested by mixtures of the Formula I compound and pymetrozine allows a substantial reduction in the application rates of one or both of these active ingredients, while maintaining good insecticidal efficacy. The greater than expected effect persists for weeks after application, facilitating long-term control. Decreasing application rates reduces treatment cost to the farmer and also eases the burden on the environment both from manufacturing waste and crop protection chemical residues.

The presence of a synergistic effect between two active ingredients is established with the aid of the Colby equation (see Colby, S. R., "Calculating Synergistic and Antagonistic Responses of Herbicide Combinations", Weeds 1967, 15, 20–22):

$$p = A + B - \left[\frac{A \times B}{100}\right]$$

Using the method of Colby, the presence of a synergistic interaction between two active ingredients is established by first calculating the predicted activity, p, of the mixture based on activities of the two components applied alone. If p is lower than the experimentally established effect, synergism is present. In the equation above, A is the insecticidal activity in percentage control of one component applied alone at rate x. The B term is the insecticidal activity in percentage control of the second component applied at rate y. The equation calculates p, the insecticidal activity of the mixture of A at rate x with B at rate y if their effects are strictly additive and no interaction has occurred.

In this invention, insecticidal activities provided by compositions of the Formula I compound and pymetrozine alone are compared with that of compositions of the Formula I compound and pymetrozine mixtures. Based on the descriptions of synergism developed by Colby, the mixtures of the present invention are found to be synergistically useful. More particularly, mixtures comprising combinations of (a) the Formula I compound and (b) pymetrozine, wherein the weight ratio of component (a) to component (b) is between about 300:1 and 1:150 can be synergistic. Preferably the weight ratio of component (a) to component (b) is between about 10:1 and 1:10, and more preferably between about 4:1 and 1:4, and most preferably between about 2:1 and 1:2. For ease of application and to obtain optimal efficacy, insecticides are typically applied formulated as agricultural compositions. This invention therefore also provides compositions comprising (a) the Formula I compound, (b) pymetrozine and (c) at least one of a surfactant, a solid diluent or a liquid diluent. Moreover, compositions comprising components (a) and (b) alone can be conveniently mixed with an optional diluent prior to applying to the crop to be protected. Through the use of these compositions, this invention also provides an improved method of combating Homopterous insects in field, vegetable, greenhouse, and orchard crops.

Mixtures of the Formula I compound and pymetrozine can be formulated in two ways:
1. the Formula I compound and pymetrozine can be formulated separately and applied separately or applied simultaneously in an appropriate weight ratio, e.g., as a tank mix; or
2. the Formula I compound and pymetrozine can be formulated together in the weight ratios as defined herein.

The insecticidal compositions of the present invention comprise an effective amount of a mixture of the Formula I compound and pymetrozine as defined above as the active ingredients and an agriculturally suitable carrier comprising at least one of a surfactant, a solid diluent or a liquid diluent consistent with the physical properties of the active ingredients, mode of application and environmental factors such as soil type, moisture and temperature. Useful formulations of the Formula I compound and pymetrozine, either separately or together, can be prepared in conventional ways. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers,* 2nd Ed., Dorland Books, Caldwell, N.J. Typical liquid diluents are described in Marsden, *Solvents Guide,* 2nd Ed., Interscience, New York, 1950. *McCutcheon's Detergents and Emulsifiers Annual,* Allured Publ. Corp., Ridgewood, N.J., as well as Sisely and Wood, *Encyclopedia of Surface Active Agents* Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, *Agglomeration, Chemical Engineering*, Dec. 4, 1967, pp 147–48, *Perry's Chemical Engineer's Handbook*, 4th Ed., McGraw-Hill, New York, (1963), pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, (1989).

In the following Examples, all percentages are by weight and all formulations are prepared in conventional ways.

Example A

Wettable Powder

| | |
|---|---|
| (S,R)-methyl 7-chloro-2,5-dihydro-2-[[(methoxycarbonyl)-[4-(trifluoromethoxy)phenyl]amino]carbonyl]indeno[1,2-e]-[1,3,4 oxadiazine-4a(3H)-carboxylate 75:25 stereoisomer mixture | 32.5% |
| pymetrozine | 32.5% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example B

Granule

| | |
|---|---|
| (S,R)-methyl 7-chloro-2,5-dihydro-2-[[(methoxycarbonyl)-[4-(trifluoromethoxy)phenyl]amino]carbonyl]indeno[1,2-e]-[1,3,4]oxadiazine-4a(3H)-carboxylate 75:25 stereoisomer mixture | 3.3% |
| pymetrozine | 6.7% |
| attapulgite granules (low volatile matter, 0.71/0.30 mm; U.S.S. No. 25-50 sieves) | 90.0%. |

Example C

Extruded Pellet

| | |
|---|---|
| methyl 7-chloro-2,5-dihydro-2-[[(methoxycarbonyl)[4-(trifluoromethoxy)phenyl]amino]carbonyl]indeno[1,2-e]-[1,3,4]oxadiazine-4a(3H)-carboxylate | 16.7% |
| pymetrozine | 8.3% |
| anhydrous sodium sulfate | 10.0% |
| crude calcium ligninsulfonate | 5.0 |
| sodium alkylnaphthalenesulfonate | 1.0% |
| calcium/magnesium bentonite | 59.0%. |

Example D

Emulsifiable Concentrate

| | |
|---|---|
| (S)-methyl 7-chloro-2,5-dihydro-2-[[(methoxycarbonyl)-[4-(trifluoromethoxy)phenyl]amino]carbonyl]indeno[1,2-e]-[1,3,4]oxadiazine-4a(3H)-carboxylate | 5.0% |
| pymetrozine | 20.0% |
| blend of oil soluble sulfonates and polyoxyethylene ethers | 10.0% |
| isophorone | 70.0%. |

Example E

Wettable Powder

| | |
|---|---|
| (S,R)-methyl 7-chloro-2,5-dihydro-2-[[(methoxycarbonyl)-[4-(trifluoromethoxy)phenyl]amino]carbonyl]indeno[1,2-e]-[1,3,4]oxadiazine-4a(3H)-carboxylate 75:25 stereoisomer mixture | 64.8% |
| pymetrozine | 0.2% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example F

Emulsifiable Concentrate

| | |
|---|---|
| (S)-methyl 7-chloro-2,5-dihydro-2-[[(methoxycarbonyl)-[4-(trifluoromethoxy)phenyl]amino]carbonyl]indeno[1,2-e]-[1,3,4]oxadiazine-4a(3H)-carboxylate | 0.2% |
| pymetrozine | 24.8% |
| blend of oil soluble sulfonates and polyoxyethylene ethers | 10.0% |
| isophorone | 70.0%. |

The mixtures of this invention are useful as insect control agents. The present invention therefore further comprises a method of controlling insects by applying to the above ground portions of the plant an effective amount of the insecticidal composition of the Formula I compound and pymetrozine. Alternatively, an insecticidal composition containing only one of the Formula I compound or pymetrozine can be applied followed by application of a composition of the other active ingredient. Furthermore, a separate composition of the Formula I compound and a composition of pymetrozine can be combined as a physical mixture prior to application, e.g., a tank mix, and applied simultaneously. The compositions of this invention provide control of insects of the order Hemiptera and Thysanoptera, and, in particular, the order Homoptera. The composition of this invention provides effective control of a broad spectrum of insect pests, particularly Homopterous pests of ornamental, vegetable, field, cereal, greenhouse, fruit and vine crops, particularly aphid pests of vegetables, fruit and cotton. These insects include *Brevicoryne brassicae, Hydaphis pseudobrassicae, Acyrthosiphon pisum, Aphis craccivora, Aphis fabae, Macrosiphum rosae, Macrosiphum euphorbiae, Hyalopterus amygdali, Brachycaudus persicaecola, Aphis pomi, Sappaphis piricola, Aphis citricola, Nasonovia ribisnigri, Eriosoma lanigerum, Megoura viciae,* Pemphigus sp., Toxoptera spp., *Phorodon humuli, Diuraphis noxia, Lipaphis erysimi, Metopolophium dirhodium,* Therioaphis spp., *Schizaphis graminum, Sitobion avenae,* Rhopalosiphum spp., *Aphis gossypii, Myzus nicotianae* and particularly *Myzus persicae*. The insects also include *Bemisia tabaci, Trialeurodes vaporariorum, Nilaparvata lugens,* Nephotettix spp., *Philaenus spumarius,* Empoasca spp., *Spissistilus festinus, Laodelphax striatellus,* Erythroneura sp., *Typhlocyba pomaria, Adelges abietis, Icerya Planococcus citri, Phenacoccus* spp., *Pseudococcus* spp., *Centrococcus sp., Eriococcus purchasi, Aonidiella aurantii, Quadraspidiotus perniciosus, Gossyparia spuria, Planococcus citri,* Phenacoccus spp., Pseudococcus spp., Centrococcus sp., *Eriococcus azaleae, Oebalus pugnax, Nezara viridula,* Lygus spp., Euschistus spp., Chlorochroa spp., Pachypsylla celtidismama, *Paratrioza cockerelli, Cacopsylla pyricola, Pseudatomoscelis seriatus,* Thrips spp., *Frankliniella occidentalis, Pineus strobi* and other genera and species closely related to these insects. As the Formula I compound and pymetrozine are believed to have different biochemical modes of action, their combinations are therefore also useful for reducing the likelihood of development of insect resistance.

The mixtures of this invention can also be further mixed with one or more other insecticides, fungicides, nematocides, bactericides, acaricides, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamectin, acephate, azinphos-methyl, bifenthrin, buprofezin, carbofuran, chlorpyrifos, chlorpyrifos-methyl, cyfluthrin, beta-cyfluthrin, deltamethrin, diafenthiuron, diazinon, diflubenzuron, dimethoate, esfenvalerate, fenpropathrin, fenvalerate, fipronil, flucythrinate, tau-fluvalinate, fonophos, imidacloprid, isofenphos, malathion, metaldehyde, methamidophos, methidathion, methoprene, methoxychlor, monocrotophos, oxamyl, parathion, parathion-methyl, permethrin, phorate, phosalone, phosmet, phosphamidon, pirimicarb, profenofos, rotenone, sulprofos, tebufenozide, tefluthrin, terbufos, tetrachlorvinphos, thiodicarb, tralomethrin, trichlorfon and triflumuron; fungicides such as azoxystrobin (ICIA5504), benomyl, blasticidin-S, Bordeaux mixture (tribasic copper sulfate), bromuconazole, captafol, captan, carbendazim, chloroneb, chlorothalonil, copper oxychloride, copper salts, cymoxanil, cyproconazole, cyprodinil (CGA 219417), diclomezine, dicloran, difenoconazole, dimethomorph, diniconazole, diniconazole-M, dodine, edifenphos, epoxyconazole (BAS 480F), fenarimol, fenbuconazole, fenpiclonil, fenpropidin, fenpropimorph, fluquinconazole, flusilazole, flutolanil, flutriafol, folpet, fosetyl-aluminum, furalaxyl, hexaconazole, ipconazole, iprobenfos, iprodione, isoprothiolane, kasugamycin, kresoxim-methyl (BAS 490F), mancozeb, maneb, mepronil, metalaxyl, metconazole, myclobutanil, neo-asozin (ferric methanearsonate), oxadixyl, penconazole, pencycuron, probenazole, prochloraz, propiconazole, pyrifenox, pyroquilon, sulfur, tebuconazole, tetraconazole, thiabendazole, thiophanate-methyl, thiram, triadimefon, triadimenol, tricyclazole, triticonazole, uniconazole, validamycin and vinclozolin; nematocides such as aldoxycarb and fenamiphos; bactericides such as streptomycin; acaricides such as amitraz, chinomethionat, chlorobenzilate, cyhexatin, dicofol, dienochlor, fenazaquin, fenbutatin oxide, fenpropathrin, fenpyroximate, hexythiazox, propargite, pyridaben and tebufenpyrad; and biological agents such as Bacillus thuringiensis, Bacillus thuringiensis delta endotoxin, baculovirus, and entomopathogenic bacteria, virus and fungi.

In certain instances, combinations with other arthropodicides having a similar spectrum of control but a different mode of action will be particularly advantageous for resistance management.

Insecticidally and arthropodicidally effective amounts of the Formula I compound, pymetrozine, and their mixtures and agricultural compositions can be influenced by many factors of the environment. Optimal rates of application are best determined under actual use conditions. Insects can normally be controlled when treated at a rate of from less than 37 g/ha to 300 g/ha of aggregate active ingredient. Aggregate active ingredient is defined as the total combined weight of active ingredients. Preferred foliar application of a composition of this invention are compositions containing 12 to 100 g/ha of the Formula I compound as (S,R)-methyl 7-chloro-2,5-dihydro-2-[[(methoxy-carbonyl)[4-(trifluoromethoxy)phenyl]amino]carbonyl]indeno[1,2-e][1,3,4]oxadiazine-4a(3H)-carboxylate 75:25 stereoisomer mixture and 25 to 200 g/ha of pymetrozine.

The following Test Examples demonstrate the mixtures, compositions and method of the present invention and provide experimental evidence for synergy between the Formula I compound and pymetrozine in controlling Myzus persicae as an example of Homopterous insects. The insect control protection afforded by these mixtures is not limited, however, to this species.

In the following Test Examples, the Formula I compound was used as the (S,R)-methyl 7-chloro-2,5-dihydro-2-[[(methoxycarbonyl)[4-(trifluoromethoxy)phenyl]-amino]carbonyl]indeno[1,2-e][1,3,4]oxadiazine4a(3H)-carboxylate 75:25 stereoisomer mixture.

Test A

Synergistic Combination of the Formula I Compound and Pymetrozine

Test compositions were prepared as follows. The Formula I compound was used as a 30% dry flowable (DF) formulation. Pymetrozine was used as 25% wettable powder (WP) formulation. The Formula I compound and pymetrozine stock solutions were prepared for testing in aqueous solution containing 500 ppm X-77 surfactant (X-77 Spreader, Loveland Industries Inc.). A stock solution of the Formula I compound was prepared by adding 167 mg of Formula I 30DF (50 mg of active ingredient) to 250 mL of surfactant/water solution to produce a Formula I compound concentration of 200 ppm. A stock solution of pymetrozine was prepared by adding 240 mg of pymetrozine 25WP (60 mg active ingredient) to 250 mL of surfactant/water solution to produce a pymetrozine concentration of 240 ppm. Concentrations for testing each compound were made by diluting an amount of stock solution with an equal amount of surfactant/water solution to create a ½ stock solution concentration. A measured portion of the stock solution was then diluted with measured amounts of surfactant/water solution to make appropriate concentrations of the stock solution. This process was continued until all the desired concentrations were made. The Formula I compound was prepared at concentrations of 200, 100, 20 and 2 ppm. Pymetrozine was prepared at concentrations of 240, 120, 60 and 20 ppm. Combination treatments were made by mixing 15 mL of a Formula I compound concentration that was twice that of the desired final concentration with 15 mL of a pymetrozine concentration that was also twice that of the desired final concentration (e.g., 15 mL of 200 ppm Formula I compound and 15 mL of 240 ppm pymetrozine to yield a total volume of 30 mL of 100 ppm Formula I compound and 120 ppm pymetrozine, etc.). Treatments of individual active ingredients were diluted to give 100, 50, 10 and 1 ppm concentrations of the Formula I compound and 120, 60, 30 and 10 ppm concentrations of pymetrozine.

An application concentration of 1 ppm in Tests A–C often corresponds to an application rate of about 6 to 12 g ai/ha in field use, but equivalent field use rates will vary considerably due to a variety of factors, including the density of vegetation to be treated. For example, the skilled artisan appreciates that treating the extensive foliage of mature trees in a orchard requires a much higher application rate per hectare than treating a seedling row crop. One skilled in the art understands these factors and can easily determine application rates necessary for the desired level of insect control.

Radish (*Raphanus sativus* L. 'Cherry Belle') seedlings (10–14 days-old, 8–12 cm tall) were used as test plants.

Radish seeds were planted in 6.25-cm² Lockwood D-902® pots (Superior Containers, Cleveland, Ohio) using Metro-Mix 350® growing medium (Grace-Sierra, Milpitas, Calif.). Twenty-four hours before infestation with aphids, each test plant was staked with a 12-cm wooden plank, trimmed of young leaves, and left with the two opposite primary leaves. The soil was covered with white-sand. The next day, both primary leaves of each test plant were infested, moderately to heavily depending on plant size, with Green peach aphids, *Myzus persicae* (Sulzer), of mixed growth stages from a lab colony reared on radish under conditions of 27±1° C., 50% relative humidity (RH), 16:8 photoperiod of hours of light and dark cycles (L:D) respectively, and 40 $\mu Em^{-2}{}_s{}^{-1}$ light intensity.

Twenty-four hours after the test plants were infested, a surfactant/water solution (50 mL) of the formulated compound was sprayed to run-off on a turntable sprayer (10 rpm) on both the upper and lower leaf surfaces using an atomizing nozzle (Spraying Systems 12244SS) at 69 kPa. Plant material and aphids were sprayed. The plants were removed from the turntable and allowed to dry. The radish plants were sprayed with the above mentioned concentrations of the Formula I compound and pymetrozine alone or with combinations of the Formula I compound and pymetrozine at all concentration combinations.

The test units, pots and plants, were held in a growth chamber with holding conditions set to 25±2° C., 50% RH, 16:8 (L:D), 40 $\mu Em^{-2}{}_s{}^{-1}$ light intensity. The test units were maintained for 48 h post-treatment after which the number of dead (immobile, deformed, badly convulsing) and live aphids were counted. For each test unit, all aphids were counted on the plants, the support system for the plants, and on the sand surface. The percentage mortality was calculated for each test unit by the following formula.

$$\% \text{ Mortality} = \left[\frac{\text{number of dead aphids}}{\text{(number of dead aphids + number of live aphids)}}\right] \times 100\%$$

There were three replications of each treatment, and an average percentage mortality was determined for each treatment.

The mean percentage aphid mortality at 48 hours post-treatment is summarized in Table 1. The results demonstrate consistent synergism for mixtures of the Formula I compound and pymetrozine.

TABLE 1

Synergistic Effect of Formula I/Pymetrozine Combinations on *Myzus persicae*

| Concentration (ppm ai)* | | % Aphid Control | |
|---|---|---|---|
| Formula I | Pymetrozine | Observed† | Expected‡ |
| Alone | | | |
| 1 | 0 | 17 | — |
| 10 | 0 | 38 | — |
| 50 | 0 | 58 | — |
| 100 | 0 | 60 | — |
| 0 | 10 | 34 | — |
| 0 | 30 | 36 | — |
| 0 | 60 | 35 | — |
| 0 | 120 | 36 | — |
| Mixtures | | | |
| 1 | 10 | 34 | 45 |
| 1 | 30 | 50 | 47 |

TABLE 1-continued

Synergistic Effect of Formula I/Pymetrozine Combinations on *Myzus persicae*

| Concentration (ppm ai)* | | % Aphid Control | |
|---|---|---|---|
| Formula I | Pymetrozine | Observed† | Expected‡ |
| 1 | 60 | 60 | 46 |
| 1 | 120 | 56 | 47 |
| 10 | 10 | 91 | 59 |
| 10 | 30 | 87 | 60 |
| 10 | 60 | 93 | 60 |
| 10 | 120 | 87 | 60 |
| 50 | 10 | 97 | 72 |
| 50 | 30 | 97 | 73 |
| 50 | 60 | 96 | 73 |
| 50 | 120 | 97 | 73 |
| 100 | 10 | 100 | 74 |
| 100 | 30 | 97 | 74 |
| 100 | 60 | 92 | 74 |
| 100 | 120 | 98 | 76 |

*Concentration of active ingredient applied.
†Mean actual observed percentage mortality.
‡Expected mortality calculated from Colby equation.

Test B

Synergistic Combination of the Formula I Compound and Pymetrozine

Test compositions were prepared as follows. The Formula I compound was in a 30% dry flowable (DF) formulation. Pymetrozine was used as 25% wettable powder (WP) formulation. The Formula I compound and pymetrozine stock solutions were prepared for testing in 500 ppm X-77 surfactant/water solution. A stock solution of the Formula I compound was made by adding 27.4 mg of Formula I 30DF (8.2 mg of active ingredient) to 164 mL of surfactant/water solution to produce a Formula I compound concentration of 50 ppm. A stock solution of pymetrozine was made by adding 32.9 mg of pymetrozine 25WP (10 mg active ingredient) to 164 mL of surfactant/water solution to produce a pymetrozine concentration of 50 ppm.

The composition prepared above was tested as follows. The test conditions were identical as those described for Test A except that (i) the test concentrations of the Formula I compound were 0.1, 1, 5, 10 and 25 ppm and (ii) the test concentrations for pymetrozine were 0.1, 1, 5, 10 and 25 ppm.

The mean percentage aphid mortality at 48 hours post-treatment is summarized in Table 2. This test shows the synergism illustrated in Test A also occurs at lower application rates of the Formula I compound and pymetrozine.

TABLE 2

Synergistic Effect of Formula I/Pymetrozine Combinations on *Myzus persicae*

| Concentration (ppm ai)* | | % Aphid Control | |
|---|---|---|---|
| Formula I | Pymetrozine | Observed† | Expected‡ |
| Alone | | | |
| 0.1 | 0 | 14 | — |
| 1 | 0 | 25 | — |
| 5 | 0 | 39 | — |
| 10 | 0 | 76 | — |
| 25 | 0 | 78 | — |
| 0 | 0.1 | 20 | — |
| 0 | 1 | 26 | — |
| 0 | 5 | 39 | — |

TABLE 2-continued

Synergistic Effect of Formula I/Pymetrozine Combinations on *Myzus persicae*

| Concentration (ppm ai)* | | % Aphid Control | |
|---|---|---|---|
| Formula I | Pymetrozine | Observed† | Expected‡ |
| 0 | 10 | 46 | — |
| 0 | 25 | 50 | — |
| Mixtures | | | |
| 0.1 | 0.1 | 35 | 31 |
| 0.1 | 1 | 25 | 36 |
| 0.1 | 5 | 47 | 48 |
| 0.1 | 10 | 34 | 54 |
| 0.1 | 25 | 45 | 57 |
| 1 | 0.1 | 81 | 40 |
| 1 | 1 | 49 | 45 |
| 1 | 5 | 56 | 54 |
| 1 | 10 | 59 | 59 |
| 1 | 25 | 54 | 63 |
| 5 | 0.1 | 87 | 51 |
| 5 | 1 | 92 | 55 |
| 5 | 5 | 88 | 63 |
| 5 | 10 | 94 | 67 |
| 5 | 25 | 94 | 70 |
| 10 | 0.1 | 93 | 81 |
| 10 | 1 | 100 | 82 |
| 10 | 5 | 93 | 85 |
| 10 | 10 | 97 | 87 |
| 10 | 25 | 93 | 88 |
| 25 | 0.1 | 94 | 82 |
| 25 | 1 | 99 | 84 |
| 25 | 5 | 96 | 87 |
| 25 | 10 | 96 | 88 |
| 25 | 25 | 97 | 89 |

*Concentration of active ingredient applied.
†Mean actual observed percentage mortality.
‡Expected mortality calculated from Colby equation.

Test C

Synergistic Interaction between the Formula I Compound and pymetrozine

Test compositions were prepared as follows. The Formula I compound was in a 30% dry flowable (DF) formulation. Pymetrozine was used as 25% wettable powder (WP) formulation. The Formula I compound and pymetrozine stock solutions were prepared for testing in 500 ppm X-77 surfactant/water solution. A stock solution of the Formula I compound was made by adding 27.4 mg of Formula I 30DF (8.2 mg of active ingredient) to 164 mL of surfactant/water solution to produce a Formula I compound concentration of 50 ppm. A stock solution of pymetrozine was made by adding 32.9 mg of pymetrozine 25WP (10 mg active ingredient) to 164 mL of surfactant/water solution to produce a pymetrozine concentration of 50 ppm.

The test composition and conditions were identical as those described for Test B. Thus, the rates of the two component compounds in the mixture were: 0.1, 1, 5, 10 and 25 ppm for both Formula I and pymetrozine, respectively. There were four replications of each treatment.

The mean percentage aphid mortality at 48 hours post-treatment is summarized in Table 3. In this test, concentrations of the Formula I compound at between 1 and 25 ppm gave a pronounced significant synergistic interaction on the effect of pymetrozine.

TABLE 3

Synergistic Effect of Formula I/Pymetrozine Combinations on *Myzus persicae*

| Concentration (ppm ai)* | | % Aphid Control | |
|---|---|---|---|
| Formula I | Pymetrozine | Observed† | Expected‡ |
| Alone | | | |
| 0.1 | 0 | 2 | — |
| 1 | 0 | 5 | — |
| 5 | 0 | 15 | — |
| 10 | 0 | 30 | — |
| 25 | 0 | 40 | — |
| 0 | 0.1 | 20 | — |
| 0 | 1 | 48 | — |
| 0 | 5 | 52 | — |
| 0 | 10 | 51 | — |
| 0 | 25 | 70 | — |
| Mixtures | | | |
| 0.1 | 0.1 | 13 | 22 |
| 0.1 | 1 | 14 | 49 |
| 0.1 | 5 | 24 | 53 |
| 0.1 | 10 | 19 | 52 |
| 0.1 | 25 | 24 | 71 |
| 1 | 0.1 | 52 | 24 |
| 1 | 1 | 77 | 51 |
| 1 | 5 | 73 | 54 |
| 1 | 10 | 48 | 54 |
| 1 | 25 | 41 | 72 |
| 5 | 0.1 | 73 | 32 |
| 5 | 1 | 92 | 56 |
| 5 | 5 | 70 | 49 |
| 5 | 10 | 86 | 58 |
| 5 | 25 | 79 | 75 |
| 10 | 0.1 | 85 | 44 |
| 10 | 1 | 96 | 64 |
| 10 | 5 | 95 | 66 |
| 10 | 10 | 86 | 66 |
| 10 | 25 | 90 | 79 |
| 25 | 0.1 | 99 | 52 |
| 25 | 1 | 98 | 69 |
| 25 | 5 | 98 | 71 |
| 25 | 10 | 98 | 71 |
| 25 | 25 | 98 | 82 |

*Concentration of active ingredient applied.
†Mean actual observed percentage mortality.
‡Expected mortality calculated from Colby equation.

What is claimed is:

1. A insecticidal mixture comprising synergistic insecticidally effective amounts of the compound of Formula I

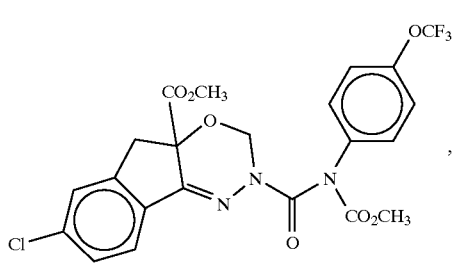

which is methyl 7-chloro-2,5-dihydro-2-[[(methoxycarbonyl)[4-(trifluoromethoxy)-phenyl]amino]carbonyl]indeno[1,2-e][1,3,4]oxadiazine-4a(3H)-carboxylate, and the compound of Formula II

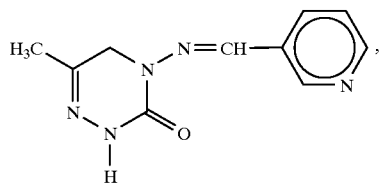

which is (E)-4,5-dihydro-6-methyl-4-[(3-pyridinylmethylene)amino]-1,2,4-triazin-3(2H)-one (pymetrozine), wherein the weight ratio of the Formula I compound to the Formula II compound is between about 300:1 and 1:150.

2. An insecticidal composition comprising an insecticidally effective amount of a mixture of claim 1 and at least one of the following: surfactant, solid or liquid diluent.

3. A method for controlling insects comprising contacting the insects or their environment with a synergistic insecticidally effective amount of the mixture of claim 1 or composition of claim 2.

4. A method of claim 3 wherein the insects to be controlled are aphids.

5. A method for controlling insects comprising applying sequentially in any order to the insects or their environment a synergistic insecticidally effective amount of a first composition comprising methyl 7-chloro-2,5-dihydro-2-[[(methoxycarbonyl)-[4-(trifluoromethoxy)phenyl]amino]carbonyl]indeno[1,2-e][1,3,4]oxadiazine-4a(3H)-carboxylate and at least one of a surfactant, a solid diluent or a liquid diluent; and a synergistic insecticidally effective amount of a second composition comprising pymetrozine and at least one of a surfactant, a solid diluent or a liquid diluent, wherein the weight ratio of methyl 7-chloro-2,5-dihydro-2-[[(methoxycarbonyl)[4-(trifluoromethoxy)phenyl]amino]carbonyl]indeno[1,2-e][1,3,4]oxadiazine-4a(3H)-carboxylate to pymetrozine is between about 300:1 and 1:150.

6. A method for controlling insects comprising applying synergistic insecticidally effective amount of a physical mixture of a first composition comprising methyl 7-chloro-2,5-dihydro-2-[[(methoxycarbonyl)[4-(trifluoromethoxy)phenyl]amino]carbonyl]indeno[1,2-e]-[1,3,4]oxadiazine-4a(3H)-carboxylate and at least one of a surfactant, a solid diluent or a liquid diluent; and a second composition comprising pymetrozine and at least one of a surfactant, a solid diluent or a liquid diluent, wherein the weight ratio of methyl 7-chloro-2,5-dihydro-2-[[(methoxycarbonyl)[4-(trifluoromethoxy)phenyl]amino]carbonyl]indeno[1,2-e][1,3,4]oxadiazine-4a(3H)-carboxylate to pymetrozine is between about 300:1 and 1:150.

* * * * *